(12) United States Patent
Uekawa et al.

(10) Patent No.: US 8,263,797 B2
(45) Date of Patent: Sep. 11, 2012

(54) METHOD FOR PRODUCING CYCLOPROPANE CARBOXYLIC ACID COMPOUND AND INTERMEDIATE THEREFOR

(75) Inventors: Toru Uekawa, Toyonaka (JP); Jun Ohshita, Nishinomiya (JP); Kouji Yoshikawa, Toyonaka (JP); Ichiro Komoto, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 280 days.

(21) Appl. No.: 12/811,970

(22) PCT Filed: Dec. 22, 2008

(86) PCT No.: PCT/JP2008/073901
§ 371 (c)(1),
(2), (4) Date: Jul. 7, 2010

(87) PCT Pub. No.: WO2009/087941
PCT Pub. Date: Jul. 16, 2009

(65) Prior Publication Data
US 2010/0280267 A1   Nov. 4, 2010

(30) Foreign Application Priority Data
Jan. 10, 2008  (JP) .................. 2008-002988

(51) Int. Cl.
C07C 253/30  (2006.01)
C07C 255/31  (2006.01)
(52) U.S. Cl. ........................ 558/379; 558/434
(58) Field of Classification Search ............... 558/379, 558/434
See application file for complete search history.

(56) References Cited

U.S. PATENT DOCUMENTS
| | | | |
|---|---|---|---|
| 6,441,220 B1 | 8/2002 | Souda et al. | |
| 6,909,013 B2 | 6/2005 | Souda et al. | |
| 2003/0195119 A1 | 10/2003 | Mori | |

FOREIGN PATENT DOCUMENTS
| | | | |
|---|---|---|---|
| JP | 38-2272 B1 | | 3/1963 |
| JP | 2001-058971 A | | 3/2001 |
| JP | 2002-293759 A | | 10/2002 |
| JP | 2004-002363 A | | 1/2004 |
| JP | 2004002363 A | * | 1/2004 |

OTHER PUBLICATIONS

Basavaiah et al. "Applications of Baylis-Hillman coupling products: a remarkable reversal of stereochemistry from esters to nitriles: a simple synthesis of (2E)-2-methylalk-2-en-1-ols and (2Z)-2-methylalk-2-enenitriles " J Chem. Soc. Chem. Comm., 1992, pp. 955-957.*
D. Basavaiah, et al., "Applications of Baylis-Hillman Coupling Products: a Remarkable Reversal of Stereochemicsty from Esters to Nitriles: a Simple Sythesis of (2E)-2-Methyl-2-alken-1-ols and (2Z)-2-Methylalk-2-enenitriles," J. Chem. Soc., Chem. Commun. 1992, pp. 955-957, No. 13, Scheme 1.
The Chemical Society of Japan, 4th edition, Jikken Kagaku Koza 22-San-Amino-san-Peptide-Maruzen Co., Ltd., 1992, pp. 6-11.
Kagaku Daijiten Henshu Iinkai, Kagaku Daijiten 5 reduced-size edition, Kyoritsu Shuppan Co., Ltd., 1989 Nen, pp. 51-52.

* cited by examiner

*Primary Examiner* — Joseph Kosack
(74) *Attorney, Agent, or Firm* — Sughrue Mion, PLLC

(57) ABSTRACT

A method for producing a cyclopropanecarboxylic acid compound represented by formula (VI)

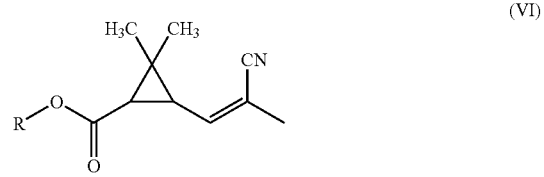

(wherein R denotes the same as below), which comprising reacting a compound represented by formula (V)

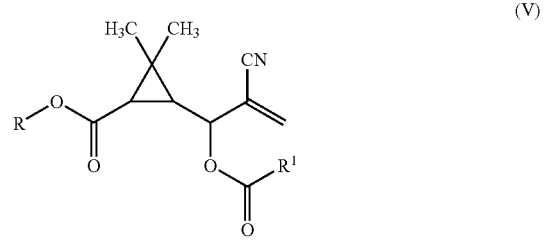

(wherein R denotes a chain hydrocarbon group having 1 to 10 carbon atoms or the like, and $R^1$ denotes a chain hydrocarbon group having 1 to 10 carbon atoms optionally substituted with a halogen atom or the like) with an alkali metal borohydride compound in the presence of a solvent.

24 Claims, No Drawings

METHOD FOR PRODUCING CYCLOPROPANE CARBOXYLIC ACID COMPOUND AND INTERMEDIATE THEREFOR

TECHNICAL FIELD

The present invention relates to a method for producing a cyclopropanecarboxylic acid compound and an intermediate thereof.

BACKGROUND ART

In U.S. Patent Laid-Open Publication No. 2003/0195119, it is disclosed that a cyclopropanecarboxylic acid compound represented by formula (VI)

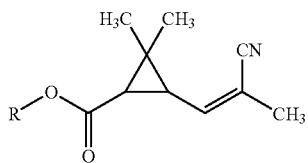

(VI)

(wherein R denotes a chain hydrocarbon group having 1 to 10 carbon atoms which is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, a cyclic hydrocarbon group having 3 to 10 carbon atoms, or a hydrogen atom) is useful as a pest control agent and an intermediate thereof, and a reaction of the corresponding cyclopropane carbaldehyde compound and diethyl(1-cyanoethyl)phosphonate is disclosed therein as a producing method therefor.

DISCLOSURE OF THE INVENTION

The present invention provides:
<1> A method for producing a cyclopropanecarboxylic acid compound represented by formula (VI)

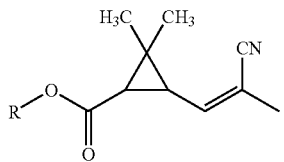

(VI)

(wherein R denotes the same as below),
which comprising reacting a compound represented by formula (V)

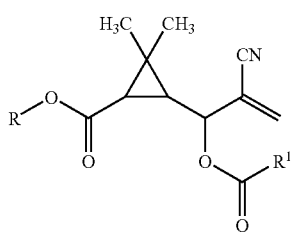

(V)

(wherein R denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, a cyclic hydrocarbon group having 3 to 10 carbon atoms, or a hydrogen atom, and $R^1$ denotes a chain hydrocarbon group having 1 to 10 carbon atoms which group is optionally substituted with a halogen atom or a phenyl group)
with an alkali metal borohydride compound in the presence of a solvent;

<2> The method according to <1>, wherein the alkali metal borohydride compound is sodium borohydride;

<3> The method according to <1> or <2>, wherein the solvent is at least one selected from the group consisting of an ether solvent, an amide solvent, a heteroaromatic solvent, a sulfur-containing aliphatic solvent, a nitrile solvent, a cyclic urea solvent, an alcohol solvent and an ester solvent;

<4> The method according to <1> or <2>, wherein the solvent is N,N-dimethylformamide, dimethylacetamide, dimethylsulfoxide, N-methyl-2-pyrrolidone, acetonitrile or 1,3-dimethyl-2-imidazolidinone;

<5> The method according to any one of <1> to <4>, wherein the compound represented by formula (V) is a compound obtained by reacting a compound represented by formula (II)

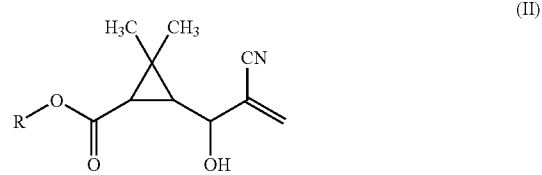

(II)

(wherein R denotes the same meaning as defined in <1>) with an acyl halide compound represented by formula (III)

(III)

(wherein $R^1$ denotes the same meaning as defined in <1> and X denotes a halogen atom)
or an acid anhydride represented by formula (IV)

(IV)

(wherein $R^1$ denotes the same meaning as defined in <1> in the presence of a base;

<6> The method according to <1>, wherein the compound represented by formula (II) is a compound obtained by reacting a compound represented by formula (I)

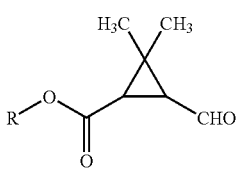

(I)

(wherein R denotes the same meaning as defined in <1>) with acrylonitrile in the presence of a base;

<7> A compound represented by formula (II)

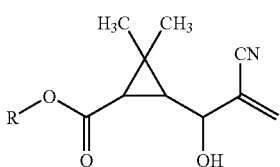

(II)

(wherein R denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, a cyclic hydrocarbon group having 3 to 10 carbon atoms, or a hydrogen atom);

<8> The compound according to <7>, wherein R is a chain hydrocarbon group having 1 to 10 carbon atoms or a chain hydrocarbon group having 1 to 10 carbon atoms which group is substituted with an optionally substituted phenyl group.

<9> The compound according to <7>, wherein R is a methyl group or a 2,3,5,6-tetrafluoro-4-methoxymethylbenzyl group;

<10> A compound represented by formula (V)

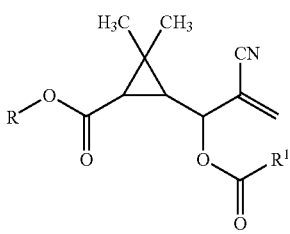

(V)

(wherein R denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, a cyclic hydrocarbon group having 3 to 10 carbon atoms, or a hydrogen atom, and $R^1$ denotes a chain hydrocarbon group having 1 to 10 carbon atoms which group is optionally substituted with a halogen atom or a phenyl group);

<11> The compound according to <10>, wherein $R^1$ is a chain hydrocarbon group having 1 to 10 carbon atoms;

<12> The compound according to <10>, wherein $R^1$ is a methyl group;

<13> The compound according to any one of <10> to <12>, wherein R is a chain hydrocarbon group having 1 to 10 carbon atoms or a chain hydrocarbon group having 1 to 10 carbon atoms which group is substituted with an optionally substituted phenyl group;

<14> The compound according to any one of <10> to <12>, wherein R is a methyl group or a 2,3,5,6-tetrafluoro-4-methoxymethylbenzyl group;

<15> A method for producing a cyclopropanecarboxylic acid compound represented by formula (IX)

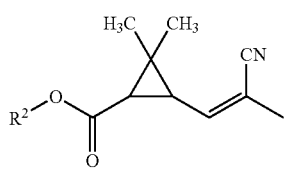

(IX)

(wherein $R^2$ denotes the same as below), which comprises reacting a compound represented by formula (Va)

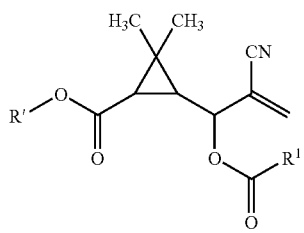

(Va)

(wherein R' denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or a cyclic hydrocarbon group having 3 to 10 carbon atoms, and $R^1$ denotes a chain hydrocarbon group having 1 to 10 carbon atoms which group is optionally substituted with a halogen atom, or a phenyl group)

with an alkali metal borohydride compound in the presence of a solvent to obtain a cyclopropanecarboxylic acid compound represented by formula (VIa)

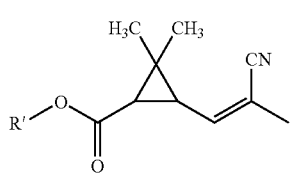

(VIa)

(wherein R' denotes the same as above), and reacting the obtained cyclopropanecarboxylic acid compound represented by formula (VIa) with a compound represented by formula (VIII)

$R^2$—OH          (VIII)

(wherein $R^2$ is different from the R' and denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or a cyclic hydrocarbon group having 3 to 10 carbon atoms)
in the presence of an alkali metal hydroxide;

<16> The method according to <15>, wherein the alkali metal hydroxide is lithium hydroxide;

<17> The method according to <15> or <16>, wherein the solvent is at least one selected from the group consisting of an ether solvent, an amide solvent, a heteroaromatic solvent, a sulfur-containing aliphatic solvent, a nitrile solvent, a cyclic urea solvent, an alcohol solvent and an ester solvent;

<18> A method for producing a cyclopropanecarboxylic acid represented by formula (VII)

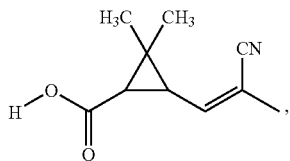

(VII)

which comprises reacting a compound represented by formula (Va)

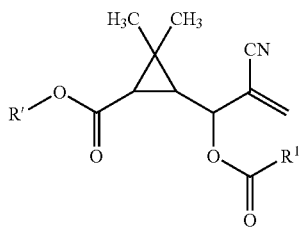

(Va)

(wherein R' denotes the same as below)
with an alkali metal borohydride compound in the presence of a solvent to obtain a cyclopropanecarboxylic acid compound represented by formula (VIa)

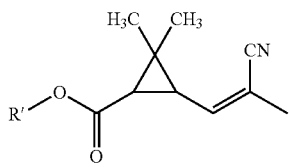

(VIa)

(wherein R' denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or a cyclic hydrocarbon group having 3 to 10 carbon atoms, and $R^1$ denotes a chain hydrocarbon group having 1 to 10 carbon atoms which group is optionally substituted with a halogen atom, or a phenyl group), and hydrolyzing the obtained cyclopropanecarboxylic acid compound represented by formula (VIa);

<19> The method according to <18>, wherein the solvent is at least one selected from the group consisting of an ether solvent, an amide solvent, a heteroaromatic solvent, a sulfur-containing aliphatic solvent, a nitrile solvent, a cyclic urea solvent, an alcohol solvent and an ester solvent;

<20> A method for producing a cyclopropanecarboxylic acid compound represented by formula (IX)

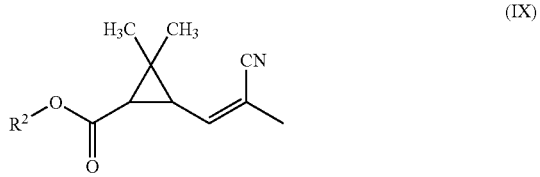

(IX)

(wherein $R^2$ denotes the same as below), which comprises preparing the cyclopropanecarboxylic acid represented by formula (VII) by the method according to <18> or <19>, and then reacting the obtained cyclopropanecarboxylic acid represented by formula (VII) with a compound represented by formula (VIII)

$R^2$—OH    (VIII)

(wherein $R^2$ is different from the R' and denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or a cyclic hydrocarbon group having 3 to 10 carbon atoms)
in the presence of a zirconium compound;

<21> The method according to <20>, wherein the zirconium compound is zirconium tetrahalide, a zirconocene compound or a zirconium alkoxide;

<22> A method for producing a cyclopropanecarboxylic acid compound represented by formula (IXa)

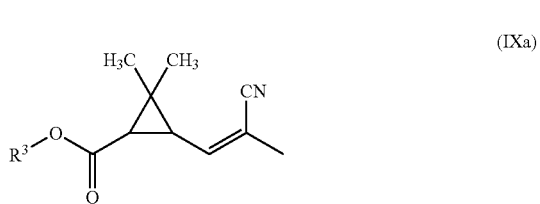

(IXa)

(wherein $R^3$ denotes the same as below), which comprises reacting a compound represented by formula (Vb)

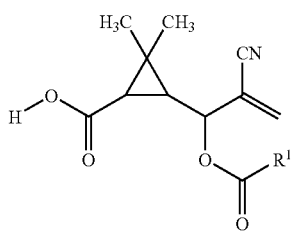

(wherein R¹ denotes a chain hydrocarbon group having 1 to 10 carbon atoms which group is optionally substituted with a halogen atom, or a phenyl group)
with an alkali metal borohydride compound in the presence of a solvent to obtain a cyclopropanecarboxylic acid compound represented by formula (VIb)

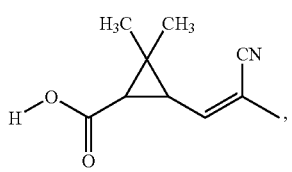

and
reacting the obtained cyclopropanecarboxylic acid compound represented by formula (VIb) with a compound represented by formula (VIIIa)

 (VIIIa)

(wherein R³ denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or a cyclic hydrocarbon group having 3 to 10 carbon atoms) in the presence of a zirconium compound;

<23> The method according to <22>, wherein the zirconium compound is zirconium tetrahalide, a zirconocene compound or a zirconium alkoxide.

<24> The method according to <22>, wherein the solvent is at least one selected from the group consisting of an ether solvent, an amide solvent, a heteroaromatic solvent, a sulfur-containing aliphatic solvent, a nitrile solvent, a cyclic urea solvent, an alcohol solvent and an ester solvent; and the like.

BEST MODE FOR CARRYING OUT THE INVENTION

A compound of the present invention, represented by formula (V)

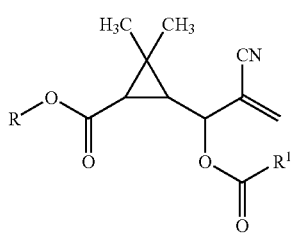

(hereinafter briefly referred to as the compound (V)), is a novel compound, in the formula, R denotes a chain hydrocarbon group having 1 to 10 carbon atoms optionally substituted with at least one group selected from the group consisting of a halogen atom, an optionally substituted acyl group having 2 to 7 carbon atoms, an optionally substituted alkoxy group having 1 to 7 carbon atoms, an optionally substituted alkylthio group having 1 to 3 carbon atoms and an optionally substituted phenyl group,
a cyclic hydrocarbon group having 3 to 10 carbon atoms, or a hydrogen atom, and
R¹ denotes a chain hydrocarbon group having 1 to 10 carbon atoms which group is optionally substituted with a halogen atom or a phenyl group.

Examples of the chain hydrocarbon group having 1 to 10 carbon atoms include a methyl group, an ethyl group, a propyl group, a butyl group, a tert-butyl group, a 2-propenyl group and a propargyl group.

Examples of the halogen atom include a fluorine atom, a bromine atom and a chlorine atom.

Examples of the optionally substituted acyl group having 2 to 7 carbon atoms include unsubstituted acyl groups having 2 to 7 carbon atoms, such as an acetyl group, a propionyl group and a benzoyl group, and acyl groups having 2 to 7 carbon atoms substituted with a halogen atom, such as a para-bromobenzoyl group.

Examples of the optionally substituted alkoxy group having 1 to 7 carbon atoms include unsubstituted alkoxy groups having 1 to 7 carbon atoms, such as a methoxy group, an ethoxy group, a propoxy group, an isopropoxy group, a butoxy group and an isobutoxy group, and alkoxy groups having 1 to 7 carbon atoms substituted with a phenyl group, such as a benzyloxy group.

Examples of the optionally substituted alkylthio group having 1 to 3 carbon atoms include unsubstituted alkylthio groups having 1 to 3 carbon atoms, such as a methylthio group and an ethylthio group.

Examples of the optionally substituted phenyl group include a phenyl group; and phenyl groups substituted with at least one selected from the group consisting of a halogen atom, an alkoxy group having 1 to 7 carbon atoms, an alkoxyalkyl group having 2 to 7 carbon atoms, a nitro group and an acyl group having 2 to 10 carbon atoms, such as a 4-bromobenzyl group, a 4-methoxyphenyl group, a 2,3-difluorophenyl group, a 2,3,5-trifluorophenyl group, a 2,3,5,6-tetrafluoro-4-methoxymethylphenyl group, a 2-nitrophenyl group, a 4-nitrophenyl group and an anthraquinone-2-yl group.

Examples of the chain hydrocarbon group having 1 to 10 carbon atoms substituted with at least one group selected from the group consisting of a halogen atom, an optionally substituted acyl group having 2 to 7 carbon atoms, an optionally substituted alkoxy group having 1 to 7 carbon atoms, an optionally substituted alkylthio group having 1 to 3 carbon atoms and an optionally substituted phenyl group include a 2-chloroethyl group, a 2,2,2-trichloroethyl group, a phenacyl group, a para-bromophenacyl group, a methoxymethyl group, a methoxymethoxymethyl group, a benzyloxymethyl group, a methylthiomethyl group, a 2-methylthioethyl group, a benzyl group, a phenethyl group, a 4-bromobenzyl group, a 4-methoxybenzyl group, a 2,3-difluorobenzyl group, a 2,3,5-trifluorobenzyl group, a 2,3,5,6-tetrafluoro-4-methoxymethylbenzyl group, a 2-nitrobenzyl group, a 4-nitrobenzyl group, a bis(ortho-nitrophenyl)methyl group and an (anthraquinone-2-yl)methyl group.

Examples of the cyclic hydrocarbon group having 3 to 10 carbon atoms include a cyclopropyl group, a cyclopentyl group and a cyclohexyl group.

Among these groups denoted by R, a chain hydrocarbon group having 1 to 10 carbon atoms or a chain hydrocarbon group having 1 to 10 carbon atoms substituted with an optionally substituted phenyl group is preferable; and a methyl group or a 2,3,5,6-tetrafluoro-4-methoxymethylbenzyl group is more preferable.

In the above-mentioned formula (V), examples of the chain hydrocarbon group having 1 to 10 carbon atoms optionally substituted with a halogen atom, denoted by $R^1$, include chain hydrocarbon groups having 1 to 10 carbon atoms, such as a methyl group, an ethyl group, a propyl group, an allyl group and a propargyl group; and chain hydrocarbon groups having 1 to 10 carbon atoms substituted with a halogen atom, such as a 2-chloroethyl group and a 2,2,2-trichloroethyl group. Among them, chain hydrocarbon groups having 1 to 10 carbon atoms are preferable and a methyl group is more preferable.

Examples of the compound (V) include methyl
3-(1-acetoxy-2-cyano-2-propenyl)-2,2-dimethylcyclopropanecarboxylate, ethyl
3-(1-acetoxy-2-cyano-2-propenyl)-2,2-dimethylcyclopropanecarboxylate, propyl
3-(1-acetoxy-2-cyano-2-propenyl)-2,2-dimethylcyclopropanecarboxylate, 2-propenyl
3-(1-acetoxy-2-cyano-2-propenyl)-2,2-dimethylcyclopropanecarboxylate, methoxymethyl
3-(1-acetoxy-2-cyano-2-propenyl)-2,2-dimethylcyclopropanecarboxylate, phenacyl
3-(1-acetoxy-2-cyano-2-propenyl)-2,2-dimethylcyclopropanecarboxylate, benzyl
3-(1-acetoxy-2-cyano-2-propenyl)-2,2-dimethylcyclopropanecarboxylate, 2,3,5,6-tetrafluoro-4-methoxymethylbenzyl
3-(1-acetoxy-2-cyano-2-propenyl)-2,2-dimethylcyclopropanecarboxylate, para-nitrobenzyl
3-(1-acetoxy-2-cyano-2-propenyl)-2,2-dimethylcyclopropanecarboxylate, bis(ortho-nitrophenyl)methyl
3-(1-acetoxy-2-cyano-2-propenyl)-2,2-dimethylcyclopropanecarboxylate, methyl
3-(1-chloroacetoxy-2-cyano-2-propenyl)-2,2-dimethylcyclopropanecarboxylate, methyl
3-(1-trichloroacetoxy-2-cyano-2-propenyl)-2,2-dimethylcyclopropanecarboxylate, methyl
3-(1-butyryloxy-2-cyano-2-propenyl)-2,2-dimethylcyclopropanecarboxylate, methyl
3-(1-propionyloxy-2-cyano-2-propenyl)-2,2-dimethylcyclopropanecarboxylate, methyl
3-(1-pivaloyloxy-2-cyano-2-propenyl)-2,2-dimethylcyclopropanecarboxylate, methyl
3-(1-benzoyloxy-2-cyano-2-propenyl)-2,2-dimethylcyclopropanecarboxylate, 2,3,5,6-tetrafluoro-4-methoxymethylbenzyl
3-(1-propionyloxy-2-cyano-2-propenyl)-2,2-dimethylcyclopropanecarboxylate, 2,3,5,6-tetrafluoro-4-methoxymethylbenzyl
3-(1-pivaloyloxy-2-cyano-2-propenyl)-2,2-dimethylcyclopropanecarboxylate and 2,3,5,6-tetrafluoro-4-methoxymethylbenzyl
3-(1-benzoyloxy-2-cyano-2-propenyl)-2,2-dimethylcyclopropanecarboxylate.

A cyclopropanecarboxylic acid compound represented by formula (VI) (hereinafter briefly referred to as the compound (VI))

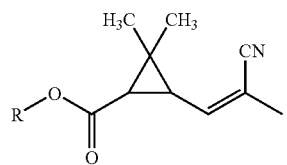

(VI)

(wherein R denotes the same as above)
may be produced by reacting the compound (V) with an alkali metal borohydride compound in the presence of a solvent.

Examples of the alkali metal borohydride compound include lithium borohydride, sodium borohydride, potassium borohydride, potassium tri-sec-butylborohydride and sodium cyanoborohydride; and sodium borohydride is preferable.

The used amount of the alkali metal borohydride compound is not limited as long as it is an amount such that the amount of a hydrogen atom bonded to a boron atom in the alkali metal borohydride compound is 1 mol or more with respect to 1 mol of the compound (V). Practically, the amount of a hydrogen atom bonded to a boron atom in the alkali metal borohydride compound is 1 to 20 mol with respect to 1 mol of the compound (V). When sodium borohydride having four hydrogen atoms each bonded to a boron atom is used as the alkali metal borohydride compound, the used amount thereof is practically 0.3 to 5 mol with respect to 1 mol of the compound (V). When potassium tri-sec-butylborohydride having one hydrogen atom bonded to a boron atom is used as the borohydride compound, the used amount thereof is practically 1 to 20 mol with respect to 1 mol of the compound (V).

The reaction of the compound (V) and the alkali metal borohydride compound (hereinafter briefly referred to as a reduction reaction) is performed in the presence of a solvent.

Examples of the solvent include an ether solvent, an amide solvent, a heteroaromatic solvent, a sulfur-containing aliphatic solvent, a nitrile solvent, a cyclic urea solvent, an alcohol solvent, an ester solvent and an aromatic hydrocarbon solvent. The solvents may be used singly or as a mixture of two kinds or more. Another solvent inactive in the reduction reaction may be used together with these solvents.

Examples of the ether solvent include diethyl ether, tert-butyl methyl ether, cyclopentyl methyl ether, tetrahydrofuran, 1,4-dioxane and 2,3-dihydrofuran; examples of the amide solvent include N,N-dimethylformamide, N,N-dimethylacetamide and N-methyl-2-pyrrolidone; and examples of the heteroaromatic solvent include pyridine and pyrrole.

Examples of the sulfur-containing aliphatic solvent include dimethyl sulfoxide and sulfolane; examples of the nitrile solvent include acetonitrile, propionitrile, ethylene cyanohydrin, chloroacetonitrile and benzonitrile; and examples of the cyclic urea solvent include 1,3-dimethyl-2-imidazolidinone.

Examples of the alcohol solvent include methanol, ethanol, 2-propanol and polyethylene glycol; and examples of the ester solvent include methyl acetate, ethyl acetate and butyl acetate.

Examples of the aromatic hydrocarbon solvent include chlorobenzene.

In view of the yield and Z-isomer/E-isomer ratio of the compound (VI), at least one solvent selected from the group consisting of an ether solvent, an amide solvent, a heteroaromatic solvent, a sulfur-containing aliphatic solvent, a nitrile solvent, a cyclic urea solvent, an alcohol solvent and an ester solvent is preferable, at least one solvent selected from the group consisting of an amide solvent, a sulfur-containing aliphatic solvent, a nitrile solvent, a cyclic urea solvent, an alcohol solvent and an ester solvent is more preferable, and at least one solvent selected from the group consisting of an amide solvent, a sulfur-containing aliphatic solvent and a cyclic urea solvent is particularly preferable. Among them, N,N-dimethylformamide, N,N-dimethylacetamide, dimethyl sulfoxide, N-methyl-2-pyrrolidone, acetonitrile and 1,3-dimethyl-2-imidazolidinone are preferable, and N-methyl-2-pyrrolidone and 1,3-dimethyl-2-imidazolidinone are more preferable.

In this specification, a compound in which the cyano group is positioned on the same side as the cyclopropane ring in the carbon-carbon double bond moiety bonded to the cyclopropane ring of the compound (VI) is referred to as "Z-isomer". A compound in which the cyano group is positioned on the opposite side to the cyclopropane ring in the carbon-carbon double bond moiety is referred to as "E-isomer".

The used amount of the solvent is ordinarily 0.5 to 30 parts by weight with respect to 1 part by weight of the compound (V).

The reduction reaction is performed by mixing the solvent, the compound (V) and the alkali metal borohydride compound. The mixing order of them is not limited, but the compound (V) is preferably added to a mixture of the alkali metal borohydride compound and the solvent in view of operation and reaction control.

The reaction temperature of the reduction reaction is ordinarily −50 to 100° C., preferably −20 to 30° C. The reaction time of the reduction reaction is ordinarily 5 minutes to 72 hours.

The progress of the reduction reaction may be confirmed by an ordinary means such as gas chromatography or high-performance liquid chromatography.

After completion of the reduction reaction, a mixture containing the compound (VI) is obtained. The mixture is subjected to ordinary post-treatment such as neutralization, extraction or water washing, and ordinary isolation treatment such as distillation or crystallization to take out the compound (VI). The obtained compound (VI) may be further purified by an ordinary purification means such as recrystallization; extraction purification; distillation; adsorption treatment with activated carbon, silica or alumina; or chromatography such as silica gel column chromatography.

Examples of the compound (VI) thus obtained include 3-(2-cyano-1-propenyl)-2,2-dimethylcyclopropanecarboxylic acid, methyl 3-(2-cyano-1-propenyl)-2,2-dimethylcyclopropanecarboxylate, ethyl 3-(2-cyano-1-propenyl)-2,2-dimethylcyclopropanecarboxylate, propyl 3-(2-cyano-1-propenyl)-2,2-dimethylcyclopropanecarboxylate, 2-propenyl 3-(2-cyano-1-propenyl)-2,2-dimethylcyclopropanecarboxylate, methoxymethyl 3-(2-cyano-1-propenyl)-2,2-dimethylcyclopropanecarboxylate, phenacyl 3-(2-cyano-1-propenyl)-2,2-dimethylcyclopropanecarboxylate, benzyl 3-(2-cyano-1-propenyl)-2,2-dimethylcyclopropanecarboxylate, 2,3,5,6-tetrafluoro-4-methoxymethylbenzyl 3-(2-cyano-1-propenyl)-2,2-dimethylcyclopropanecarboxylate, para-nitrobenzyl 3-(2-cyano-1-propenyl)-2,2-dimethylcyclopropanecarboxylate and bis(ortho-nitrophenyl)methyl 3-(2-cyano-1-propenyl)-2,2-dimethylcyclopropanecarboxylate.

The compound (V) may be produced by reacting a compound represented by formula (II) (hereinafter briefly referred to as the compound (II))

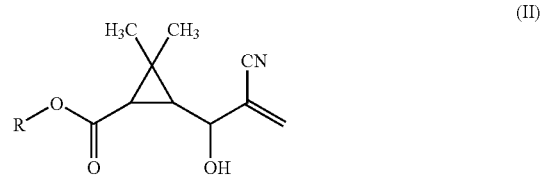

(wherein R denotes the same as above) with an acyl halide compound represented by formula (III) (hereinafter briefly referred to as the acyl halide compound (III))

(wherein $R^1$ denotes the same as above and X denotes a halogen atom) or an acid anhydride represented by formula (IV) (hereinafter briefly referred to as the acid anhydride (IV))

(wherein $R^1$ denotes the same as above) in the presence of a base. The acyl halide compound (III) and the acid anhydride (IV) are sometimes collectively referred to as an "acylating agent". The reaction of the compound (II) and the acylating agent is hereinafter referred to as an "acylating reaction".

Examples of the compound (II) include
3-(2-cyano-1-hydroxy-2-propenyl)-2,2-dimethylcyclopropanecarboxylic acid, methyl
3-(2-cyano-1-hydroxy-2-propenyl)-2,2-dimethylcyclopropanecarboxylate, ethyl
3-(2-cyano-1-hydroxy-2-propenyl)-2,2-dimethylcyclopropanecarboxylate, propyl
3-(2-cyano-1-hydroxy-2-propenyl)-2,2-dimethylcyclopropanecarboxylate, 2-propenyl
3-(2-cyano-1-hydroxy-2-propenyl)-2,2-dimethylcyclopropanecarboxylate, methoxymethyl
3-(2-cyano-1-hydroxy-2-propenyl)-2,2-dimethylcyclopropanecarboxylate, phenacyl
3-(2-cyano-1-hydroxy-2-propenyl)-2,2-dimethylcyclopropanecarboxylate, benzyl
3-(2-cyano-1-hydroxy-2-propenyl)-2,2-dimethylcyclopropanecarboxylate, 2,3,5,6-tetrafluoro-4-methoxymethylbenzyl
3-(2-cyano-1-hydroxy-2-propenyl)-2,2-dimethylcyclopropanecarboxylate, para-nitrobenzyl
3-(2-cyano-1-hydroxy-2-propenyl)-2,2-dimethylcyclopropanecarboxylate and bis(ortho-nitrophenyl)methyl
3-(2-cyano-1-hydroxy-2-propenyl)-2,2-dimethylcyclopropanecarboxylate.

In the formula (III), examples of the halogen atom denoted by X include a chlorine atom, a bromine atom and an iodine atom.

Examples of the acyl halide compound (III) include acetyl chloride, acetyl bromide, chloroacetyl chloride, trichloroacetyl chloride, propionyl chloride, propionyl fluoride, butanoyl chloride, pivaloyl chloride, benzoyl chloride and benzoyl bromide.

Examples of the acid anhydride (IV) include acetic anhydride, propionic anhydride, butyric anhydride, isobutyric anhydride, hexanoic anhydride, valeric anhydride, chloroacetic anhydride, trifluoroacetic anhydride and benzoic anhydride.

As for these acylating agents, commercial acylating agents may be adopted, or acylating agents produced by known methods such as a method of halogenating a corresponding carboxylic acid and a method of dehydrating a corresponding carboxylic acid.

The used amount of the acylating agent is ordinarily 1 to 5 mol with respect to 1 mol of the compound (II).

Examples of the base include basic nitrogen-containing compounds such as triethylamine, pyridine, N,N-diethylaniline, 4-dimethylaminopyridine, diisopropylethylamine and tetramethylethylenediamine; alkali metal alkoxides such as sodium methoxide; carboxylates such as sodium acetate; alkali metal hydroxides such as sodium hydroxide and potassium hydroxide; and alkali metal carbonates such as potassium carbonate. Basic nitrogen-containing compounds are preferable, and triethylamine, pyridine, N,N-diethylaniline, 4-dimethylaminopyridine and diisopropylethylamine are more preferable. These bases may be used singly or as a mixture of two kinds or more.

The used amount of the base is not limited and may be a catalytic amount or an excessive amount over the compound (II). Practically, the used amount is 0.01 to 3 mol with respect to 1 mol of the compound (II).

The acylating reaction may be performed in the presence of a solvent. Examples of the solvent include aromatic hydrocarbon solvents such as benzene, toluene and xylene; aliphatic hydrocarbon solvents such as hexane and heptane; ether solvents such as diethyl ether, tert-butyl methyl ether, cyclopentyl methyl ether, tetrahydrofuran and 1,4-dioxane; halogenated hydrocarbon solvents such as dichloromethane, 1,2-dichloroethane and chlorobenzene; ketone solvents such as methyl isobutyl ketone; nitro solvents such as nitromethane and nitrobenzene; nitrile solvents such as acetonitrile, propionitrile and benzonitrile; and amide solvents such as dimethylformamide and dimethylacetamide. These solvents may be used singly or as a mixture of two kinds or more. The used amount of the solvent is ordinarily 0.2 to 20 parts by weight with respect to 1 part by weight of the compound (II).

The acylating reaction is performed by mixing the compound (II), the acylating agent and the base in the presence of a solvent as required, and the mixing order of them is not limited.

The reaction temperature of the acylating reaction is ordinarily −20 to 100° C., preferably −5 to 100° C. The reaction time of the acylating reaction is ordinarily 5 minutes to 72 hours.

The progress of the acylating reaction may be confirmed by an ordinary means such as gas chromatography or high-performance liquid chromatography.

After completion of the acylating reaction, a reaction mixture containing the compound (V) is obtained. The mixture is subjected to ordinary post-treatment such as neutralization, extraction or water washing, and ordinary isolation treatment such as distillation or crystallization to take out the compound (V). The compound (V) taken out may be further purified by an ordinary purification means such as recrystallization; extraction purification; distillation; adsorption treatment with activated carbon, silica or alumina; or chromatography such as silica gel column chromatography. The compound (V) taken out may be used for the reduction reaction, or the purified compound (V) may be used for the reduction reaction. The obtained reaction mixture containing the compound (V) may be directly used for the above-mentioned reduction reaction, or the reaction mixture may be used for the reduction reaction after being subjected to ordinary post-treatment such as neutralization, extraction or water washing.

The compound (II) may be produced by reacting a compound represented by formula (I) (hereinafter briefly referred to as the compound (I))

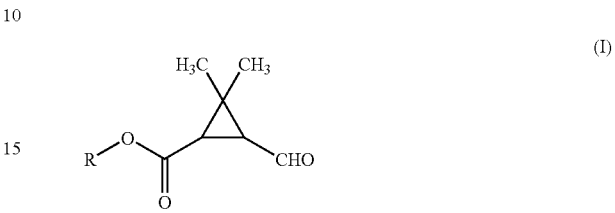

(wherein R denotes the same as above) with acrylonitrile in the presence of a base. The reaction of the compound (I) and acrylonitrile is hereinafter referred to as a "coupling reaction".

Examples of the compound (I) include 3-formyl-2,2-dimethylcyclopropanecarboxylic acid, methyl 3-formyl-2,2-dimethylcyclopropanecarboxylate, ethyl 3-formyl-2,2-dimethylcyclopropanecarboxylate, propyl 3-formyl-2,2-dimethylcyclopropanecarboxylate, 2-propenyl 3-formyl-2,2-dimethylcyclopropanecarboxylate, methoxymethyl 3-formyl-2,2-dimethylcyclopropanecarboxylate, phenacyl 3-formyl-2,2-dimethylcyclopropanecarboxylate, benzyl 3-formyl-2,2-dimethylcyclopropanecarboxylate, 2,3,5,6-tetrafluoro-4-methoxymethylbenzyl 3-formyl-2,2-dimethylcyclopropanecarboxylate, para-nitrobenzyl 3-formyl-2,2-dimethylcyclopropanecarboxylate and bis(ortho-nitrophenyl) methyl 3-formyl-2,2-dimethylcyclopropanecarboxylate.

The compound (I) may be produced by known methods described in Japanese Laid-open Patent Publication No. 2004-2363 and Japanese Laid-open Patent Publication No. 2006-89427.

As acrylonitrile, commercial acrylonitrile is ordinarily adopted.

The used amount of acrylonitrile is ordinarily 0.8 to 5 mol, preferably 1 to 3 mol with respect to 1 mol of the compound (I).

Examples of the base used for the coupling reaction include basic nitrogen-containing compounds such as trimethylamine, triethylamine, pyridine, 4-dimethylaminopyridine, 1,8-diazabicycloundecene, 1,4-diazabicyclo[2,2,2]octane, quinuclidine, 3-hydroxyquinuclidine, indolizine, tetramethylguanidine, imidazole and 1-methylimidazole. Among them, trimethylamine, triethylamine, 1,8-diazabicyclo[5,4,0]-7-undecene and 1,4-diazabicyclo[2,2,2]octane are preferable. As the base, a commercial base is ordinarily adopted.

The used amount of the base is not limited and may be a catalytic amount or an excessive amount over the compound (I); practically, the used amount is 0.1 to 3 mol with respect to 1 mol of the compound (I).

The coupling reaction is ordinarily performed in the presence of a solvent. Examples of the solvent include aromatic hydrocarbon solvents such as benzene, toluene and xylene; aliphatic hydrocarbon solvents such as hexane and heptane; ether solvents such as diethyl ether, tert-butyl methyl ether, cyclopentyl methyl ether, tetrahydrofuran and 1,4-dioxane; halogenated hydrocarbon solvents such as dichloromethane, 1,2-dichloroethane and chlorobenzene; ketone solvents such as acetone, methyl isobutyl ketone and cyclohexanone; ester solvents such as methyl acetate, ethyl acetate and butyl acetate; nitro solvents such as nitromethane and nitrobenzene; nitrile solvents such as acetonitrile, propionitrile and benzonitrile; amide solvents such as dimethylformamide and dimethylacetamide; alcohol solvents such as methanol, ethanol, 1-propanol and 2-propanol; and water. These solvents may be used singly or as a mixture of two kinds or more.

The used amount of the solvent is ordinarily 0.05 to 3 parts by weight with respect to 1 part by weight of the compound (I).

The coupling reaction is performed by mixing the compound (I), acrylonitrile and the base in the presence of a solvent as required, and the mixing order of them is not limited.

The reaction temperature of the coupling reaction is ordinarily −20 to 100° C., preferably −5 to 100° C. The reaction time of the coupling reaction is ordinarily 5 minutes to 72 hours.

The progress of the coupling reaction may be confirmed by an ordinary means such as gas chromatography or high-performance liquid chromatography.

After completion of the reaction, a reaction mixture containing the compound (II) is obtained. The mixture is subjected to ordinary post-treatment such as neutralization, extraction or water washing, and ordinary isolation treatment such as distillation or crystallization to take out the compound (II). The compound (II) taken out may be further purified by an ordinary purification means such as recrystallization; extraction purification; distillation; adsorption treatment with activated carbon, silica or alumina; or chromatography such as silica gel column chromatography. The compound (II) taken out may be used for the acylating reaction, or the purified compound (II) may be used for the acylating reaction. The obtained reaction mixture containing the compound (II) may be directly used for the above-mentioned acylating reaction, or the reaction mixture may be used for the acylating reaction after being subjected to ordinary post-treatment such as neutralization, extraction or water washing.

With the use of a compound represented by the following formula (Va)

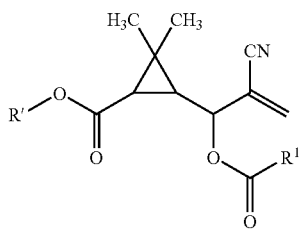

(wherein R' denotes a chain hydrocarbon group having 1 to 10 carbon atoms optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or a cyclic hydrocarbon group having 3 to 10 carbon atoms, and $R^1$ denotes the same as above) as the compound (V), a cyclopropanecarboxylic acid compound represented by formula (VIa) (hereinafter briefly referred to as the compound (VIa))

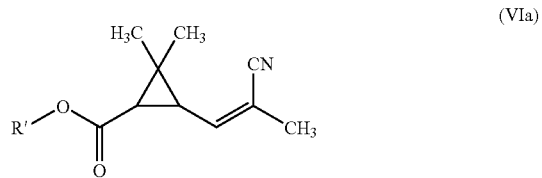

(wherein R' denotes the same as above) is obtained by performing the above-mentioned reduction reaction, and then a cyclopropanecarboxylic acid compound represented by formula (IX) (hereinafter briefly referred to as the compound (IX))

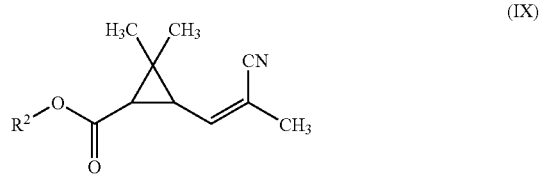

(wherein $R^2$ denotes the same as below) may be produced by reacting the obtained compound (VIa) with a compound represented by formula (VIII) (hereinafter briefly referred to as the compound (VIII))

(wherein $R^2$ is different from the R' and denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or a cyclic hydrocarbon group having 3 to 10 carbon atoms) in the presence of an alkali metal hydroxide.

Examples of R' in the compound (VIa) include the same as those mentioned for R.

Examples of the alkali metal hydroxide include lithium hydroxide, sodium hydroxide, potassium hydroxide, rubidium hydroxide, cesium hydroxide and francium hydroxide; lithium hydroxide, sodium hydroxide and potassium hydroxide are preferable, and lithium hydroxide is more preferable. As the alkali metal hydroxide, an anhydride is ordinarily adopted and a hydrate such as lithium hydroxide monohydrate may be adopted.

The used amount of the alkali metal hydroxide is not limited and is ordinarily 0.001 to 200% by mol, preferably 0.1 to 10% by mol with respect to 1 mol of the compound (VIa).

Examples of $R^2$ in the compound (VIII) include the same as those mentioned for R, and $R^2$ is a different group from R'.

Examples of the compound (VIII) include 2-chloroethanol, 2,2,2-trichloroethanol, benzoylmethanol, para-bromobenzoylmethanol, methoxymethanol, methoxymethoxymethanol, benzyloxymethanol, methylthiomethanol, 2-methylthioethanol, benzyl alcohol, phenethyl alcohol, 4-bromobenzyl alcohol, 4-methoxybenzyl alcohol, 2,3-difluorobenzyl alcohol, 2,3,5-trifluorobenzyl alcohol, 2,3,5,6-tetrafluoro-4-methoxymethylbenzyl alcohol, 2-nitrobenzyl alcohol, 4-nitrobenzyl alcohol, bis(ortho-nitrophenyl)methanol and (anthraquinone-2-yl)methanol.

The used amount of the compound (VIII) is not limited and is ordinarily 0.5 to 3 mol with respect to 1 mol of the compound (VIa). The used amount may be a greatly excessive amount as required and the compound (VIII) may also be used as a solvent.

The reaction of the compound (VIa) and the compound (VIII) is ordinarily performed under an inert gas atmosphere such as an argon or nitrogen atmosphere. The reaction may be performed under normal pressure, with pressure applied or under reduced pressure; preferably, under normal pressure or reduced pressure. The reaction is an equilibrium reaction and is preferably performed while removing by-product alcohol derived from the compound (VIa) out of the system by a method such as distillation.

The reaction may be performed without a solvent or with a solvent. Examples of the solvent include halogenated hydrocarbon solvents such as dichloromethane, chloroform and 1,2-dichloroethane; aliphatic hydrocarbon solvents such as hexane, heptane, octane and nonane; aromatic hydrocarbon solvents such as benzene, toluene, xylene and chlorobenzene; and ether solvents such as diethyl ether, methyl tert-butyl ether, cyclopentyl methyl ether, tetrahydrofuran and 1,4-dioxane. The reaction may be performed while the by-product alcohol is removed as an azeotropic mixture out of the system by using a solvent capable of forming an azeotropic mixture with the by-product alcohol derived from the compound (VIa).

The reaction temperature is not limited; preferably, 20 to 200° C.

After completion of the reaction, for example, the obtained reaction mixture is washed in water or an acidic aqueous solution such as an aqueous sulfuric acid solution to take out the compound (IX) by concentration. The compound (IX) taken out may be further purified by an ordinary purification means such as distillation, recrystallization or column chromatography.

A cyclopropanecarboxylic acid represented by formula (VII) (hereinafter briefly referred to as the carboxylic acid (VII))

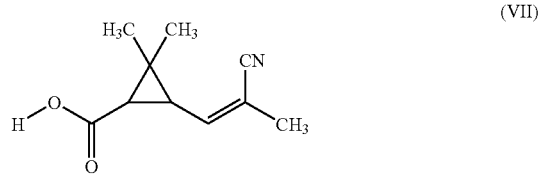
(VII)

may be produced by hydrolyzing the obtained compound (VIa).

The hydrolysis reaction of the compound (VIa) may be performed in the presence of an alkali or an acid. Examples of the alkali include alkali metal hydroxides such as sodium hydroxide and potassium hydroxide. The used amount of the alkali is ordinarily 0.5 to 20 mol, preferably 1 to 10 mol with respect to 1 mol of the compound (VIa). Examples of the acid include mineral acids such as sulfuric acid and hydrochloric acid. The used amount of the acid is ordinarily 0.5 to 20 mol, preferably 1 to 10 mol with respect to 1 mol of the compound (VIa).

For the hydrolysis reaction of the compound (VIa), 1 mol or more of water is ordinarily used with respect to 1 mol of the compound (VIa). Water may be used as a solvent. A solvent except water may be used; examples of the solvent include alcohol solvents such as methanol, ethanol, isopropanol, butanol, sec-butanol and tert-butanol; ether solvents such as tetrahydrofuran and 1,4-dioxane; ketone solvents such as acetone; nitro solvents such as nitromethane; nitrile solvents such as acetonitrile; and amide solvents such as dimethylformamide and dimethylacetamide. The used amount of the solvent is not limited; practically, 0.1 to 50 parts by weight, preferably 0.5 to 20 parts by weight with respect to 1 part by weight of the compound (VIa).

The reaction temperature of the hydrolysis reaction is ordinarily 0 to 100° C., preferably 20 to 80° C. The reaction time is not limited, and the point of time when the compound (VIa) disappears or the point of time when the decrease of the compound (VIa) stops may be regarded as the end point of the reaction. After completion of the reaction, the reaction mixture is subjected to ordinary post-treatment such as neutralization, extraction, water washing or concentration to take out the carboxylic acid (VII). The carboxylic acid (VII) taken out may be further purified by an ordinary purification means such as recrystallization or column chromatography.

The compound (IX) may also be produced by reacting the obtained carboxylic acid (VII) with the compound (VIII) in the presence of a zirconium compound.

A zirconium compound ordinarily exhibiting Lewis acidity is used as the zirconium compound, and a zirconium compound represented by formula (X)

$$Zr(O)_m(X^1)_n(Y^1)_{4-2-m-n} \quad (X)$$

(wherein $X^1$ and $Y^1$ each independently denote a halogen atom, an alkoxy group, an acyloxy group, an acetylacetonato group, a dialkylamino group, a cyclopentadienyl group or a pentamethylcyclopentadienyl group, m denotes 0 or 1, and n denotes 0, 1 or 2) is preferable.

Examples of the halogen atom include a fluorine atom, a chlorine atom, a bromine atom and an iodine atom, and examples of the alkoxy group include alkoxy groups having 1 to 4 carbon atoms, such as a methoxy group, an ethoxy group, a propoxy group, an isopropoxy group, a butoxy group, an isobutoxy group and a tert-butoxy group. Examples of the acyloxy group include acyloxy groups having 2 to 6 carbon atoms, such as an acetyloxy group, and examples of the dialkylamino group include amino groups substituted with two alkyl groups having 1 to 6 carbon atoms, such as a dimethylamino group, a diethylamino group and a methylethylamino group.

Examples of the zirconium compound represented by formula (X) include zirconium tetrahalides such as zirconium tetrafluoride, zirconium tetrachloride, zirconium tetrabromide and zirconium tetraiodide; zirconium carboxylates such as zirconium acetate; zirconium acetylacetonato; zirconium alkoxides such as zirconium ethoxide, zirconium isopropoxide, zirconium butoxide and zirconium tert-butoxide; zirconium oxyhalides such as zirconium oxychloride; aminozirconium such as tetrakis(dimethylamino)zirconium and tetrakis(diethylamino)zirconium; and zirconocene compounds such as zirconocene dichloride, zirconocene dimethoxide and decamethylzirconocene dichloride; and zirconium tetrahalide, zirconocene compounds and zirconium alkoxides are preferable.

As the zirconium compound, a commercial zirconium compound is ordinarily adopted. An anhydride or a hydrate may be adopted, and a complex with compounds having a coordinating property, such as tetrahydrofuran and tetramethylethylenediamine may be adopted.

The used amount of the zirconium compound is not limited; practically, 0.001 to 200% by mol, preferably 0.1 to 10% by mol with respect to 1 mol of the carboxylic acid (VII).

The used amount of the compound (VIII) is not limited and is ordinarily 0.5 to 3 mol with respect to 1 mol of the carboxylic acid (VII). The used amount may be a greatly excessive amount as required and the compound (VIII) may also be used as a solvent.

The reaction of the carboxylic acid (VII) and the compound (VIII) is ordinarily performed under an inert gas atmosphere such as an argon or nitrogen atmosphere. The reaction may be performed under normal pressure, with pressure applied or under reduced pressure; preferably, under normal pressure or reduced pressure. The reaction is preferably performed while water is removed as a by-product out of the system by a method such as distillation.

The reaction may be performed without a solvent or with a solvent. Examples of the solvent include halogenated hydrocarbon solvents such as dichloromethane, chloroform and 1,2-dichloroethane, aliphatic hydrocarbon solvents such as hexane, heptane, octane and nonane, aromatic hydrocarbon solvents such as benzene, toluene, xylene and chlorobenzene, and ether solvents such as diethyl ether, methyl tert-butyl ether, cyclopentyl methyl ether, tetrahydrofuran and 1,4-dioxane. The reaction may be performed while removing water as an azeotropic mixture out of the system by using a solvent capable of forming an azeotropic mixture with water.

The reaction temperature is not limited; ordinarily, 20 to 200° C.

After completion of the reaction, for example, the obtained reaction mixture is washed in water or an acidic aqueous solution such as an aqueous sulfuric acid solution to take out the compound (IX) by concentration. The compound (IX) taken out may be further purified by an ordinary purification means such as distillation, recrystallization or column chromatography.

With the use of a compound represented by the following formula (Vb)

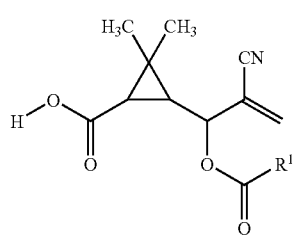
(Vb)

(wherein $R^1$ denotes the same as above) as the compound (V), a cyclopropanecarboxylic acid compound represented by formula (VIb)

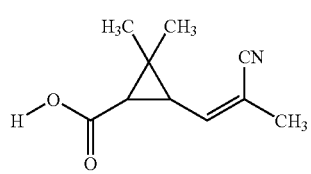
(VIb)

is obtained by performing the above-mentioned reduction reaction, and then a cyclopropanecarboxylic acid compound represented by formula (IXa)

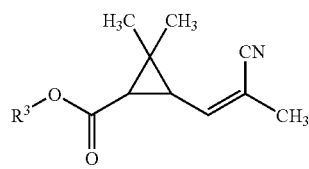
(IXa)

(wherein $R^3$ denotes the same as below) may also be produced by reacting the obtained cyclopropanecarboxylic acid compound represented by formula (VIb) with a compound represented by formula (VIIIa)

$$R^3\text{—OH} \quad \text{(VIIIa)}$$

(wherein $R^3$ denotes a chain hydrocarbon group having 1 to 10 carbon atoms optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or a cyclic hydrocarbon group having 3 to 10 carbon atoms) in the presence of a zirconium compound.

The reaction of the cyclopropanecarboxylic acid compound represented by formula (VIb) and the compound represented by formula (VIIIa) may be performed in the same manner as in the above-mentioned reaction of the carboxylic acid (VII) and the compound (VIII).

EXAMPLES

The present invention is hereinafter described by way of examples in further detail, but the invention is not limited thereto.

Example 1

26.44 g of 2,3,5,6-tetrafluoro-4-methoxymethylbenzyl (1R,3R)-3-formyl-2,2-dimethylcyclopropanecarboxylate, 8.06 g of acrylonitrile and 7.48 g of a 30% by weight aqueous solution of trimethylamine were mixed. The obtained mixture was stirred at room temperature overnight and thereafter 9 mL of methanol was added thereto. The obtained mixture was stirred at room temperature for 13 hours. Dilute hydrochloric acid was added to the obtained reaction mixture and thereafter the mixture was extracted with ethyl acetate. The obtained organic layer was washed in saturated sodium bicarbonate water and saturated saline, and thereafter dried over anhydrous sodium sulfate. After removing sodium sulfate by filtration, the obtained filtrate was concentrated under reduced pressure to obtain 30.5 g of a pale yellowish oily matter consisting essentially of a compound represented by the following formula (1) (hereinafter briefly referred to as the compound (1))

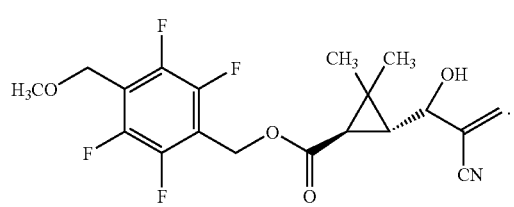
(1)

11.0 g of the obtained oily matter was purified by silica gel column chromatography to obtain 10.1 g of the compound (1).

$^1$H-NMR(CDCl$_3$, TMS) δ (ppm): 1.27 (s, 3/2H), 1.27 (s, 3/2H), 1.28 (s, 3/2H), 1.32 (s, 3/2H), 1.60-1.72 (m, 2H), 2.06 (br.d, 1/2H), 2.16 (br.d, 1/2H), 3.40 (s, 3/2H), 3.41 (s, 3/2H), 3.92 (br., 1H), 4.59 (q, 2H), 5.25-26 (m, 2H), 6.00 (d, 1/2H), 6.05 (d, 1H), 6.10 (d, 1/2H)

Example 2

19.55 g of the oily matter obtained in Example 1, 3.85 g of pyridine, 0.42 g of 4-(dimethylamino)pyridine and 80 mL of toluene were mixed. The obtained mixture was ice-cooled, into which a mixture of 4.97 g of acetic anhydride and 20 ml of toluene was dropped under a nitrogen atmosphere. After completion of dropping, the obtained mixture was stirred under ice-cooling for 1.5 hours. Water and dilute hydrochloric acid were added to the obtained reaction mixture, and the mixture was stirred and subjected to still standing and thereafter separated into an organic layer and a water layer. The obtained organic layer was washed in saturated saline and dried over anhydrous sodium sulfate. After removing sodium sulfate by filtration, the obtained filtrate was concentrated under reduced pressure to obtain 21.5 g of a pale yellowish oily matter consisting essentially of a compound represented by the following formula (2) (hereinafter briefly referred to as the compound (2))

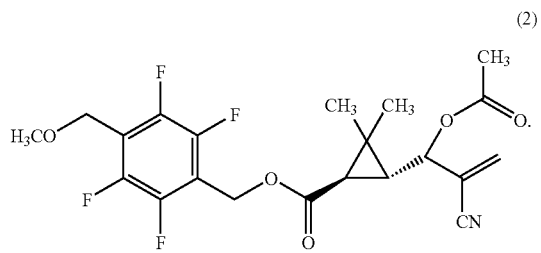

(2)

5.0 g of the obtained oily matter was purified by silica gel column chromatography to obtain 4.1 g of the compound (2).

$^1$H-NMR(CDCl$_3$, TMS) δ (ppm): 1.21 (s, 3/2H), 1.26 (s, 3/2H), 1.28 (s, 3H), 1.55 (d, 1/2H), 1.71 (d, 1/2H), 1.80 (dd, 1/2H), 1.89 (dd, 1/2H), 2.12 (s, 3/2H), 2.13 (s, 3/2H), 3.40 (s, 3/2H), 3.41 (s, 3/2H), 4.58-4.60 (m, 2H), 5.00 (d, 1/2H), 5.11 (d, 1/2H), 5.22-5.29 (m, 2H), 5.96 (d, 1/2H), 6.00 (d, 1/2H), 6.03 (d, 1/2H), 6.08 (d, 1/2H)

Example 3

0.68 g of sodium borohydride, 5 mL of hexane and 30 mL of N,N-dimethylformamide were mixed. The obtained mixture was ice-cooled, into which a mixture of 10.0 g of the pale yellowish oily matter obtained in Example 2 and 10 mL of N,N-dimethylformamide was dropped under a nitrogen atmosphere. The obtained mixture was stirred under ice-cooling for 1.5 hours. The obtained reaction mixture was added to dilute hydrochloric acid, mixed and thereafter the mixture was extracted with ethyl acetate. The obtained organic layer was washed in dilute hydrochloric acid, 3% by weight sodium bicarbonate water and 20% by weight saline, and thereafter dried over anhydrous sodium sulfate. After removing sodium sulfate by filtration, the obtained filtrate was concentrated under reduced pressure to obtain 8.1 g of a white crystal consisting essentially of a compound represented by the following formula (3) (hereinafter briefly referred to as the compound (3))

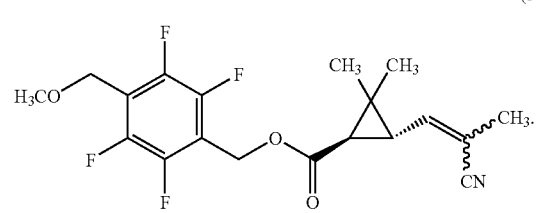

(3)

When the NMR spectrum of the crystal was measured, the Z-isomer/E-isomer ratio was about 8/1.

$^1$H-NMR(CDCl$_3$, TMS) δ (ppm): 1.21 (s, 3H, Z+E-isomer), 1.32 (s, 3H,Z+E-isomer), 1.73 (m, 1H,Z+E-isomer), 1.96 (s, 3H,Z+E-isomer), 2.20 (m, 1/9H,E-isomer), 2.47 (m, 8/9H,Z-isomer), 3.41 (s, 3H,Z+E-isomer), 4.59 (s, 2H,Z+E-isomer), 5.26 (s, 2H,Z+E-isomer), 5.78 (m, 8/9H,Z-isomer), 6.01 (m, 1/9H,E-isomer)

Example 4

31.0 g of methyl (1R,3R)-3-formyl-2,2-dimethylcyclopropanecarboxylate, 15.8 g of acrylonitrile and 19.5 g of a 30% by weight aqueous solution of trimethylamine were mixed and the obtained mixture was stirred at room temperature overnight. The obtained mixture was ice-cooled and thereafter dilute hydrochloric acid was added thereto and mixed. The obtained mixture was adjusted to room temperature and thereafter the mixture was extracted with ethyl acetate. The obtained organic layer was dried over anhydrous sodium sulfate. After removing sodium sulfate by filtration, the obtained filtrate was concentrated under reduced pressure to obtain 40.8 g of a pale yellowish oily matter consisting essentially of a compound represented by the following formula (4) (hereinafter briefly referred to as the compound (4))

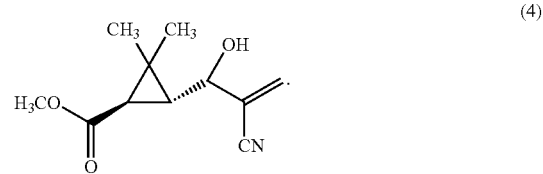

(4)

1.02 g of the obtained oily matter was purified by silica gel column chromatography to obtain 0.96 g of the compound (4). The yield was 94%.

$^1$H-NMR(CDCl$_3$, TMS) δ (ppm): 1.27 (s, 3/2H), 1.28 (s, 3/2H), 1.28 (s, 3/2H), 1.33 (s, 3/2H), 1.61-1.70 (m, 2H), 2.06 (d, 1/2H), 2.21 (d, 1/2H), 3.70 (s, 3/2H), 3.70 (s, 3/2H), 3.89-3.96 (m, 1H), 6.00 (d, 1/2H), 6.0 (d, 1/2H), 6.07 (d, 1/2H), 6.10 (d, 1/2H)

Example 5

39.8 g of the pale yellowish oily matter obtained in Example 4, 18.0 g of pyridine, 1.2 g of 4-(dimethylamino) pyridine and 200 g of toluene were mixed. The obtained mixture was ice-cooled, into which 23.3 g of acetic anhydride was dropped under a nitrogen atmosphere. After completion of dropping, the obtained mixture was stirred under ice-cooling for 1 hour. Water and 6 N hydrochloric acid were added to the obtained reaction mixture, and mixed and subjected to still standing and thereafter separated into an organic layer and a water layer. The obtained organic layer was washed in 2 N hydrochloric acid, 1 N-aqueous sodium hydroxide solution and saturated saline, and thereafter dried over anhydrous sodium sulfate. After removing sodium sulfate by filtration, the obtained filtrate was concentrated under reduced pressure to obtain 40.2 g of a pale yellowish oily matter consisting essentially of a compound represented by the following formula (5) (hereinafter briefly referred to as the compound (5))

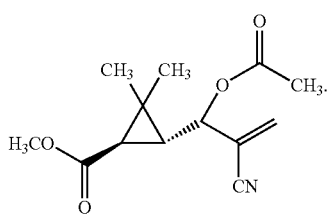

(5)

1.00 g of the obtained oily matter was purified by silica gel column chromatography to obtain 0.87 g of the compound (5).

$^1$H-NMR(CDCl$_3$, TMS) δ (ppm): 1.21 (s, 5/4H), 1.26 (s, 5/4H), 1.26 (s, 7/4H), 1.28 (s, 7/4H), 1.55 (d, 5/12H), 1.71 (d, 7/12H), 1.79 (dd, 7/12H), 1.87 (dd, 5/12H), 2.13 (s, 7/4H), 2.14 (s, 5/4H), 3.70 (s, 7/4H), 3.70 (s, 5/4H), 5.01 (d, 5/12H), 5.12 (d, 7/12H), 5.97 (d, 5/12H), 6.00 (d, 7/12H), 6.03 (d, 5/12H), 6.08 (d, 7/12H)

Example 6

50.9 g of the compound (4), 1.6 g of 4-(dimethylamino) pyridine and 176 g of toluene were mixed. The obtained mixture was ice-cooled, into which 29.5 g of acetic anhydride was dropped under a nitrogen atmosphere. After completion of dropping, the obtained mixture was stirred under ice-cooling for 8 hours. The obtained reaction mixture was washed in a 1% by weight aqueous solution of sulfuric acid, a 8% by weight aqueous solution of sodium hydroxide and water in this order, and thereafter concentrated under reduced pressure to obtain 66.9 g of a pale yellowish oily matter consisting essentially of the compound (5). When the obtained oily matter was analyzed by a gas chromatography internal standard method, the yield of the compound (5) was 88%.

Example 7

0.30 g of sodium borohydride was added little by little to a mixed solution of 1.0 g of the compound (5) and 20 mL of methanol under a nitrogen atmosphere. The obtained mixture was stirred at room temperature for 2 hours. 0.15 g of sodium borohydride was further added thereto little by little and the obtained mixture was stirred at room temperature for 1 hour. Water and 1 N hydrochloric acid were added to the obtained reaction mixture, mixed and thereafter the mixture was extracted with ethyl acetate. The obtained organic layer was washed in saturated saline and dried over anhydrous magnesium sulfate. After removing magnesium sulfate by filtration, the obtained filtrate was concentrated under reduced pressure to obtain a crude product of a compound represented by the following formula (6) (hereinafter briefly referred to as the compound (6))

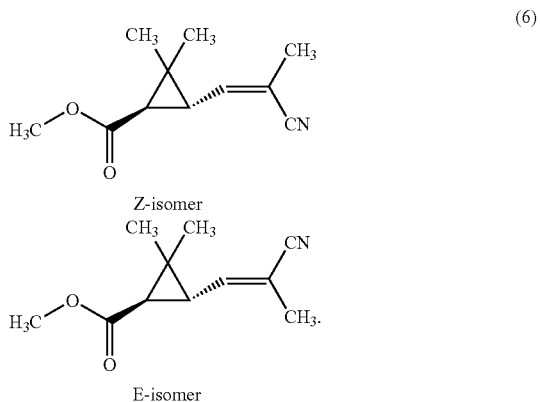

(6)

When $^1$H-NMR of the obtained crude product was measured, the Z-isomer/E-isomer ratio was 81/19. The crude product was purified by silica gel column chromatography to obtain 0.55 g of a Z-isomer and 0.12 g of an E-isomer. The total yield of the Z-isomer and E-isomer was 87% (Z-isomer/E-isomer ratio=82/18).

Z-isomer: $^1$H-NMR(CDCl$_3$, TMS) δ (ppm): 1.20 (s, 3H), 1.32 (s, 3H), 1.71 (d, 1H), 1.96 (d, 3H), 2.45 (dd, 1H), 3.70 (s, 3H), 5.80 (dd, 1H) E-isomer: $^1$H-NMR(CDCl$_3$, TMS) δ (ppm): 1.22 (s, 3H), 1.30 (s, 3H), 1.73 (d, 1H), 1.97 (d, 3H), 2.17 (dd, 1H), 3.70 (s, 3H), 6.02 (dd, 1H)

Example 8

A mixed solution of 37 mg of sodium borohydride and 4 mL of acetonitrile was cooled to −5° C. under a nitrogen atmosphere. A mixed solution of 0.25 g of the compound (5) and 1 mL of acetonitrile was dropped into the obtained mixture. The obtained mixture was stirred at −5° C. for 3 hours. Water and 1 N hydrochloric acid were added to the obtained reaction mixture, mixed and thereafter the mixture was extracted with ethyl acetate. The obtained organic layer was washed in saturated saline and dried over anhydrous magnesium sulfate. After removing magnesium sulfate by filtration, the obtained filtrate was concentrated under reduced pressure to obtain a crude product of the compound (6). When $^1$H-NMR of the obtained crude product was measured, the Z-isomer/E-isomer ratio was 87/13. The crude product was purified by silica gel column chromatography to obtain 0.13 g of a mixture of a Z-isomer and an E-isomer. The yield was 72%.

Example 9

A crude product of the compound (6) was obtained by performing the reaction in the same manner as in Example 8 except for replacing acetonitrile with N,N-dimethylformamide in Example 8. When $^1$H-NMR thereof was measured, the Z-isomer/E-isomer ratio was 92/8. The obtained crude product was purified by silica gel column chromatography to obtain 0.15 g of a mixture of a Z-isomer and an E-isomer. The yield was 78%.

Example 10

A mixed solution of 0.38 g of the compound (5) and 1.16 g of 1,3-dimethyl-2-imidazolidinone was cooled to 0° C. under a nitrogen atmosphere. 58 mg of sodium borohydride was added to the obtained mixture little by little and stirred at the same temperature. Water and 6 N hydrochloric acid were added to the obtained reaction mixture and the mixture was washed. The obtained organic layer was concentrated under reduced pressure to obtain a crude product of the compound (6). When the obtained crude product was analyzed by a gas chromatography area percentage method, the Z-isomer/E-isomer ratio was 92/8. When the crude product was analyzed by a gas chromatography internal standard method, the total yield of the Z-isomer and E-isomer was 88%.

Examples 11 to 20

A crude product of the compound (6) was obtained by performing the reaction in the same manner as in Example 10 except for replacing 1,3-dimethyl-2-imidazolidinone with solvents shown in Table 1 in Example 10. The results are shown in Table 1. In the table, the yields are the total yields of the Z-isomer and E-isomer.

TABLE 1

| Example | Solvent | Z-isomer/E-isomer ratio | Yield (%) |
|---|---|---|---|
| 11 | N,N-dimethylacetamide | 90/10 | 90 |
| 12 | dimethyl sulfoxide | 89/11 | 80 |
| 13 | polyethylene glycol (PEG200) | 85/15 | 89 |
| 14 | sulfolane | 84/16 | 79 |
| 15 | propionitrile | 83/17 | 64 |
| 16 | methyl acetate | 82/18 | 83 |
| 17 | isopropanol | 82/18 | 83 |
| 18 | pyridine | 81/19 | 70 |
| 19 | tetrahydrofuran | 79/21 | 86 |
| 20 | pyrrole | 70/30 | 92 |

Example 21

A mixed solution of 1.91 g of sodium borohydride, 41.0 g of N-methyl-2-pyrrolidone and 6.8 g of heptane was cooled to 0° C. under a nitrogen atmosphere, into which a mixed solution of 20.0 g of the compound (5) and 20.5 g of N-methyl-2-pyrrolidone was dropped and stirred at the same temperature for 1 hour. Thereafter, the reaction mixture was dropped into a 3% by weight aqueous solution of hydrochloric acid, and thereafter the obtained mixture was neutralized with a 23% by weight aqueous solution of sodium hydroxide and extracted with heptane. The obtained organic layer was sequentially washed in a 3% by weight aqueous solution of sodium hydrogen carbonate and water, and concentrated under reduced pressure to thereby obtain a crude product of the compound (6). When this crude product was analyzed by a gas chromatography area percentage method, the Z-isomer/E-isomer ratio was 92/8. When the crude product was analyzed by a gas chromatography internal standard method, the total amount of the Z-isomer and E-isomer was 13.5 g and the total yield of the Z-isomer and E-isomer was 90%.

Example 22

2.0 g of the compound (4), 0.83 g of pyridine and 20 mL of tetrahydrofuran were mixed. The obtained mixture was ice-cooled, into which 1.27 g of pivaloyl chloride was dropped under a nitrogen atmosphere. After completion of dropping, the obtained mixture was stirred under ice-cooling for about 3 hours. 0.76 g of pyridine and 1.15 g of pivaloyl chloride were added to the obtained mixture, which was further stirred under ice-cooling for about 4 hours. Water was added to the obtained reaction mixture, mixed and the mixture was extracted with ethyl acetate. The obtained organic layer was washed in dilute hydrochloric acid, saturated sodium bicarbonate water and saturated saline, and thereafter dried over anhydrous sodium sulfate. After removing sodium sulfate by filtration, the obtained filtrate was concentrated under reduced pressure. The obtained residue was purified by silica gel column chromatography to obtain 0.76 g of a compound represented by the following formula (5-2)

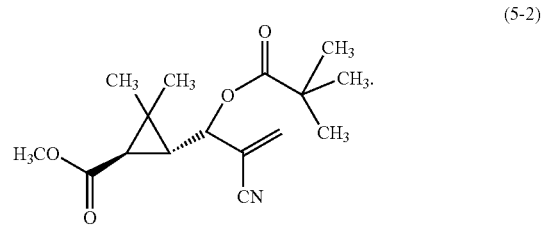

(5-2)

$^1$H-NMR(CDCl$_3$, TMS) δ (ppm): 1.19-1.29 (m, 15H), 1.59-1.68 (m, 1H), 1.77 (dd, 5/6H), 1.88 (dd, 1/6H), 3.67 (s, 5/2H), 3.70 (s, 1/2H), 4.98 (d, 1/6H), 5.15 (d, 5/6H), 5.95 (d, 1/6H), 5.98 (d, 5/6H), 6.02 (d, 1/6H), 6.07 (d, 5/6H)

Example 23

1.63 g of a compound represented by the following formula (5-3) was obtained in the same manner as in Example 22 except for replacing 1.27 g of pivaloyl chloride and 1.15 g of pivaloyl chloride with 1.48 g of benzoyl chloride and 1.34 g of benzoyl chloride, respectively in Example 22.

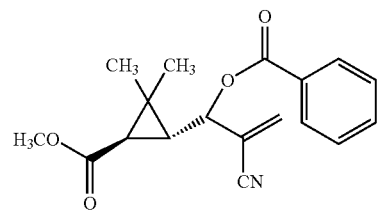

(5-3)

$^1$H-NMR(CDCl$_3$, TMS) δ (ppm): 1.24 (s, 1H), 1.28 (s, 1H), 1.30 (s, 2H), 1.35 (s, 2H), 1.66 (d, 1/3H), 1.88 (d, 2/3H), 1.95 (dd, 2/3H), 2.03 (dd, 1/3H), 3.66 (s, 2H), 3.72 (s, 1H), 5.28 (d, 1/2H), 5.39 (d, 2/3H), 6.05 (d, 1/3H), 6.06 (d, 1/3H), 6.09 (d, 2/3H), 6.12 (d, 2/3H), 7.45-7.51 (m, 2H), 7.58-7.63 (m, 1H), 8.06-8.10 (m, 2H)

Example 24

9.13 g of 2,3,5,6-tetrafluoro-4-methoxymethyl-benzyl alcohol, 7.50 g of the compound (6), 74 mg of lithium methoxide and 74 mL of heptane were mixed. The obtained mixture was refluxed for 9 hours while removing by-product methanol out of the system by azeotropy with heptane. During the reflux, 20 mL of heptane was added to the system. The amount of the mixture of methanol and heptane removed out of the system was 50 mL. The obtained reaction mixture was cooled to room temperature, and thereafter toluene and saline were added thereto, mixed and the mixture was separated. The obtained organic layer was washed in saturated saline and dried over anhydrous sodium sulfate. After removing sodium sulfate by filtration, the obtained filtrate was concentrated under reduced pressure. The obtained residue was purified by silica gel column chromatography to obtain 14.2 g of the compound (3).

Example 25

19.3 g of the compound (6), 6.0 g of sodium hydroxide, 20 mL of water and 180 mL of methanol were mixed. The obtained mixture was refluxed for 1 hour. The obtained reaction mixture was cooled to room temperature and thereafter methanol was distilled off under reduced pressure. 250 mL of water was added to the obtained residue and the obtained mixture was ice-cooled. The mixture was made to have a pH of 1 or less by adding concentrated hydrochloric acid thereto, and thereafter the mixture was extracted with ethyl acetate. The obtained organic layer was dried over magnesium sulfate. After removing magnesium sulfate by filtration, the obtained filtrate was concentrated under reduced pressure to obtain 16.9 g of a compound represented by the following formula (7) (hereinafter briefly referred to as the compound (7)). As a result of $^1$H-NMR measurement, the Z-isomer/E-isomer ratio of the product was about 8/1.

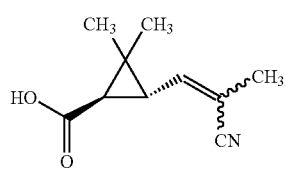
(7)

$^1$H-NMR(CDCl$_3$, TMS) δ (ppm): 1.23 (s, 8/3H), 1.24 (s, 1/3H), 1.34 (s, 1/3H), 1.36 (s, 8/3H), 1.72 (d, 8/9H), 1.74 (d, 1/9H), 1.97 (d, 8/9H), 1.97 (d, 1/9H), 2.20 (dd, 1/9H), 2.48 (dd, 8/9H), 5.82 (dq, 8/9H), 6.03 (dq, 1/9H)

Example 26

2.24 g of 2,3,5,6-tetrafluoro-4-methoxymethyl-benzyl alcohol, 70 mg of zirconium chloride and 20 mL of xylene were mixed. The obtained mixture was refluxed for about 10 minutes and thereafter 10 mL of xylene was distilled off. The obtained mixture was cooled to 80° C. and thereafter 1.97 g of the compound (7) obtained in Example 25 was added. The obtained mixture was stirred at the xylene reflux temperature for 7 hours. The operation was performed while removing by-product water out of the system by azeotropy with xylene. The obtained mixture was cooled to room temperature and thereafter washed twice in a 5% by weight aqueous solution of sulfuric acid. The obtained solution was concentrated under reduced pressure, and the obtained residue was purified by silica gel column chromatography to obtain 3.46 g of the compound (3). As a result of $^1$H-NMR measurement, the Z-isomer/E-isomer ratio of the product was about 8/1.

Example 27

8.0 g of 2,3,5,6-tetrafluoro-4-methoxymethyl-benzyl alcohol, 0.3 g of a 70% by weight zirconium tetraisopropoxide/2-propanol solution and 55 g of xylene were mixed. The obtained mixture was heated to reflux and thereafter 39 g of the distillate was removed. The obtained mixture was cooled to 80° C. and thereafter 7.4 g of the compound (7) (Z-isomer/E-isomer ratio=96/4) was added. The obtained mixture was stirred at the xylene reflux temperature for 13 hours. The operation was performed while removing by-product water out of the system by azeotropy with xylene. The obtained mixture was cooled to room temperature and thereafter 13 g of xylene was added. The obtained mixture was washed in 5% by weight sulfuric acid, a 5% by weight aqueous solution of sodium hydroxide and water, and thereafter concentrated under reduced pressure to obtain 13.4 g of the compound (3). When the compound was analyzed by a gas chromatography area percentage method, the Z-isomer/E-isomer ratio was 95/5.

Example 28

A crude product of the compound (6) was obtained by performing the reaction in the same manner as in Example 10 except for replacing 1,3-dimethyl-2-imidazolidinone with chlorobenzene in Example 10. The Z-isomer/E-isomer ratio was 65/35 and the total yield of the Z-isomer and E-isomer was 27%.

INDUSTRIAL APPLICABILITY

A compound of the present invention, represented by formula (V), is a novel compound, and a cyclopropanecarboxylic acid compound represented by formula (VI), which is a useful compound as a pest control agent and an intermediate thereof, may be produced with a favorable yield by a reaction of the compound represented by formula (V) and an alkali metal borohydride compound.

The invention claimed is:
1. A method for producing a cyclopropanecarboxylic acid compound represented by formula (VI)

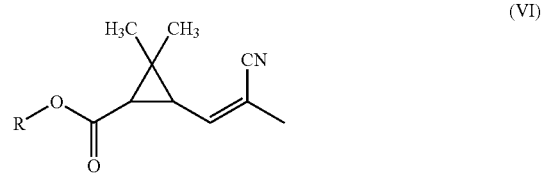
(VI)

(wherein R denotes the same as below),
which comprising reacting a compound represented by formula (V)

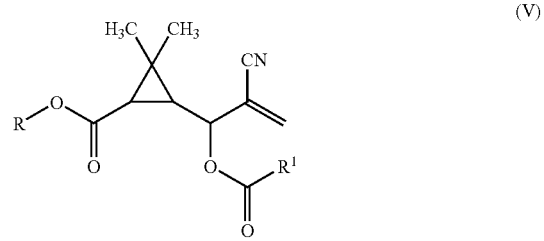
(V)

(wherein R denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group,
a cyclic hydrocarbon group having 3 to 10 carbon atoms, or a hydrogen atom, and R¹ denotes a chain hydrocarbon group having 1 to 10 carbon atoms optionally substituted with a halogen atom or a phenyl group)

with an alkali metal borohydride compound in the presence of a solvent.

2. The method according to claim 1, wherein the alkali metal borohydride compound is sodium borohydride.

3. The method according to claim 1, wherein the solvent is at least one selected from the group consisting of an ether solvent, an amide solvent, a heteroaromatic solvent, a sulfur-containing aliphatic solvent, a nitrile solvent, a cyclic urea solvent, an alcohol solvent and an ester solvent.

4. The method according to claim 1, wherein the solvent is N,N-dimethylformamide, dimethylacetamide, dimethylsulfoxide, N-methyl-2-pyrrolidone, acetonitrile or 1,3-dimethyl-2-imidazolidinone.

5. The method according to claim 1, wherein the compound represented by formula (V) is a compound obtained by reacting a compound represented by formula (II)

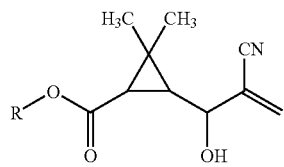
(II)

(wherein R denotes the same meaning as defined in claim 1)

with an acyl halide compound represented by formula (III)

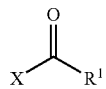
(III)

(wherein R¹ denotes the same meaning as defined in claim 1 and X denotes a halogen atom)

or an acid anhydride represented by formula (IV)

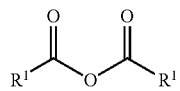
(IV)

(wherein R¹ denotes the same meaning as defined in claim 1) in the presence of a base.

6. The method according to claim 5, wherein the compound represented by formula (II) is a compound obtained by reacting a compound represented by formula (I)

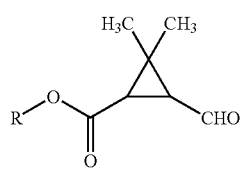
(I)

(wherein R denotes the same meaning as defined in claim 1) with acrylonitrile in the presence of a base.

7. A compound represented by formula (II)

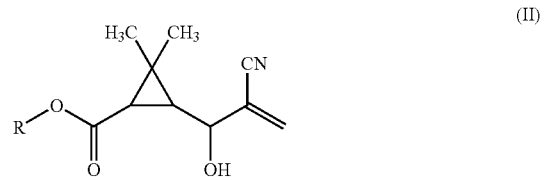
(II)

(wherein R denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, a cyclic hydrocarbon group having 3 to 10 carbon atoms, or a hydrogen atom).

8. The compound according to claim 7, wherein R is a chain hydrocarbon group having 1 to 10 carbon atoms or a chain hydrocarbon group having 1 to 10 carbon atoms which group is substituted with an optionally substituted phenyl group.

9. The compound according to claim 7, wherein R is a methyl group or a 2,3,5,6-tetrafluoro-4-methoxymethylbenzyl group.

10. A compound represented by formula (V)

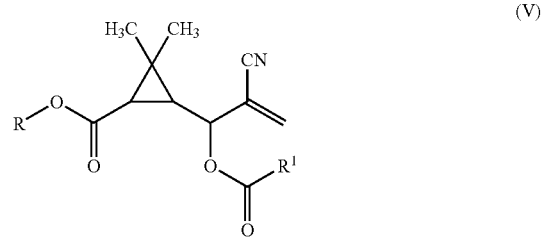
(V)

(wherein R denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, a cyclic hydrocarbon group having 3 to 10 carbon atoms or a hydrogen atom, and R¹ denotes a chain hydrocarbon group having 1 to 10 carbon atoms which group is optionally substituted with a halogen atom or a phenyl group).

11. The compound according to claim 10, wherein R¹ is a chain hydrocarbon group having 1 to 10 carbon atoms.

12. The compound according to claim 10, wherein R¹ is a methyl group.

13. The compound according to claim 10, wherein R is a chain hydrocarbon group having 1 to 10 carbon atoms or a chain hydrocarbon group having 1 to 10 carbon atoms which group is substituted with an optionally substituted phenyl group.

14. The compound according to claim 10, wherein R is a methyl group or a 2,3,5,6-tetrafluoro-4-methoxymethylbenzyl group.

15. A method for producing a cyclopropanecarboxylic acid compound represented by formula (IX)

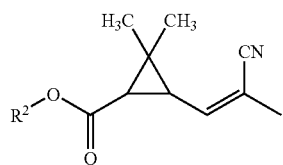

(wherein $R^2$ denotes the same as below),
which comprises reacting a compound represented by formula (Va)

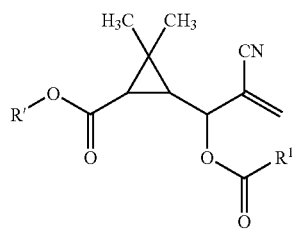

(wherein R' denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group or
a cyclic hydrocarbon group having 3 to 10 carbon atoms, and
$R^1$ denotes a chain hydrocarbon group having 1 to 10 carbon atoms optionally substituted with a halogen atom or
a phenyl group)
with an alkali metal borohydride compound in the presence of a solvent to obtain a cyclopropanecarboxylic acid compound represented by formula (VIa)

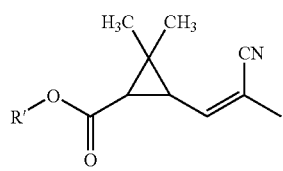

(wherein R' denotes the same as above), and
reacting the obtained cyclopropanecarboxylic acid compound represented by formula (VIa) with a compound represented by formula (VIII)

$R^2$—OH      (VIII)

(wherein $R^2$ is different from the R' and denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or
a cyclic hydrocarbon group having 3 to 10 carbon atoms)
in the presence of an alkali metal hydroxide.

16. The method according to claim 15, wherein the alkali metal hydroxide is lithium hydroxide.

17. The method according to claim 15, wherein the solvent is at least one selected from the group consisting of an ether solvent, an amide solvent, a heteroaromatic solvent, a sulfur-containing aliphatic solvent, a nitrile solvent, a cyclic urea solvent, an alcohol solvent and an ester solvent.

18. A method for producing a cyclopropanecarboxylic acid represented by formula (VII)

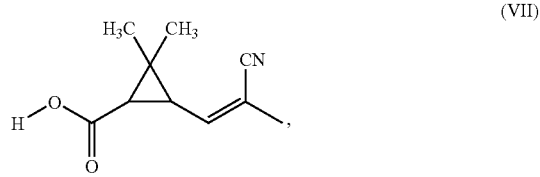

which comprises reacting a compound represented by formula (Va)

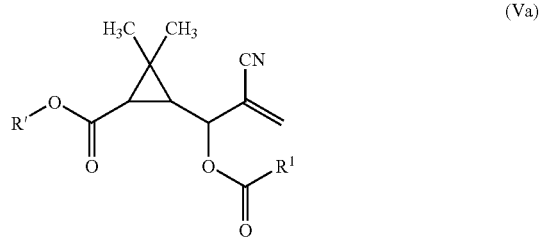

(wherein R' denotes the same as below)
with an alkali metal borohydride compound in the presence of a solvent to obtain a cyclopropanecarboxylic acid compound represented by formula (VIa)

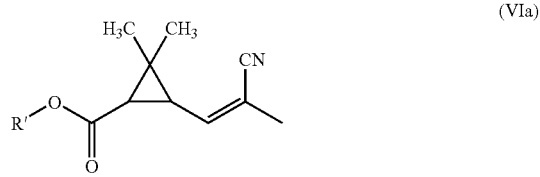

(wherein R' denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or
a cyclic hydrocarbon group having 3 to 10 carbon atoms, and
$R^1$ denotes a chain hydrocarbon group having 1 to 10 carbon atoms which group is optionally substituted with a halogen atom or a phenyl group), and hydrolyzing the obtained cyclopropanecarboxylic acid compound represented by formula (VIa).

19. The method according to claim 18, wherein the solvent is at least one selected from the group consisting of an ether solvent, an amide solvent, a heteroaromatic solvent, a sulfur-containing aliphatic solvent, a nitrile solvent, a cyclic urea solvent, an alcohol solvent and an ester solvent.

20. A method for producing a cyclopropanecarboxylic acid compound represented by formula (IX)

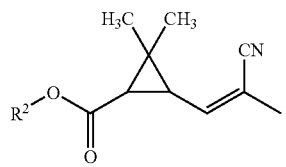

(IX)

(wherein $R^2$ denotes the same as below),
which comprises preparing the cyclopropanecarboxylic acid represented by formula (VII) by the method according to claim 18 or 19, and then reacting the obtained cyclopropanecarboxylic acid represented by formula (VII) with a compound represented by formula (VIII)

$R^2$—OH (VIII)

(wherein $R^2$ is different from the R' and denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or a cyclic hydrocarbon group having 3 to 10 carbon atoms) in the presence of a zirconium compound.

21. The method according to claim 20, wherein the zirconium compound is zirconium tetrahalide, a zirconocene compound or a zirconium alkoxide.

22. A method for producing a cyclopropanecarboxylic acid compound represented by formula (IXa)

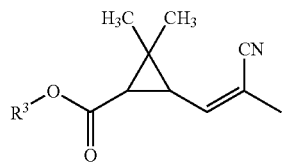

(IXa)

(wherein $R^3$ denotes the same as below),
which comprises reacting a compound represented by formula (Vb)

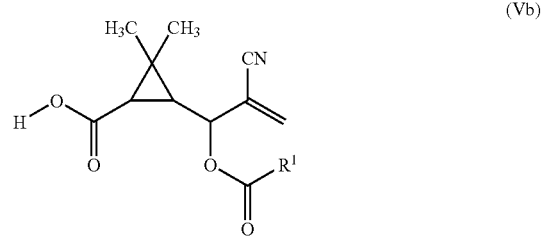

(Vb)

(wherein $R^1$ denotes a chain hydrocarbon group having 1 to 10 carbon atoms which group is optionally substituted with a halogen atom or
a phenyl group)
with an alkali metal borohydride compound in the presence of a solvent to obtain a cyclopropanecarboxylic acid compound represented by formula (VIb)

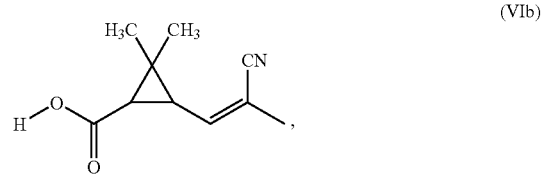

(VIb)

and
reacting the obtained cyclopropanecarboxylic acid compound represented by formula (VIb) with a compound represented by formula (VIIIa)

$R^3$—OH (VIIIa)

(wherein $R^3$ denotes a chain hydrocarbon group having 1 to 10 carbon atoms which group is optionally substituted with at least one group selected from the group consisting of a halogen atom, an acyl group having 2 to 7 carbon atoms, an optionally substituted alkoxy group having 1 to 7 carbon atoms, an optionally substituted alkylthio group having 1 to 3 carbon atoms and an optionally substituted phenyl group, or
a cyclic hydrocarbon group having 3 to 10 carbon atoms) in the presence of a zirconium compound.

23. The method according to claim 22, wherein the zirconium compound is zirconium tetrahalide, a zirconocene compound or a zirconium alkoxide.

24. The method according to claim 22, wherein the solvent is at least one selected from the group consisting of an ether solvent, an amide solvent, a heteroaromatic solvent, a sulfur-containing aliphatic solvent, a nitrile solvent, a cyclic urea solvent, an alcohol solvent and an ester solvent.

* * * * *